United States Patent [19]

Schubert et al.

[11] Patent Number: 5,576,310
[45] Date of Patent: Nov. 19, 1996

[54] 11-BENZALDOXIME-17β-METHOXY-17α-METHOXYMETHYL-ESTRASDIENE DERIVATIVES, METHODS FOR THEIR PRODUCTION AND PHARMACEUTICALS CONTAINING SUCH COMPOUNDS

[75] Inventors: Gerd Schubert; Günther Kaufmann; Lothar Sobeck; Michael Oettel, all of Jena; Walter Elger, Berlin; Anatoli Kurischko, Jena, all of Germany

[73] Assignee: Jenapharm GmbH, Jena, Germany

[21] Appl. No.: 309,270

[22] Filed: Sep. 20, 1994

[51] Int. Cl.[6] .................................................. A61K 31/56
[52] U.S. Cl. .......................... 514/179; 552/610; 552/648
[58] Field of Search ..................... 552/648, 610; 514/179

[56] References Cited

U.S. PATENT DOCUMENTS

| | | |
|---|---|---|
| 4,829,060 | 5/1989 | Ottow et al. . |
| 4,871,724 | 10/1989 | Groen et al. . |
| 4,912,097 | 3/1990 | Teutsch et al. . |
| 5,089,635 | 2/1992 | Neef et al. . |
| 5,272,140 | 12/1993 | Loozen .................... 514/172 |
| 5,276,023 | 1/1994 | Moguilewsky et al. . |
| 5,407,928 | 4/1995 | Kasch et al. . |

FOREIGN PATENT DOCUMENTS

| | | |
|---|---|---|
| 1310630 | 11/1992 | Canada . |
| 2130515 | 3/1995 | Canada . |
| 2130516 | 3/1995 | Canada . |

*Primary Examiner*—Kimberly J. Prior
*Attorney, Agent, or Firm*—Fliesler, Dubb, Meyer & Lovejoy LLP

[57] ABSTRACT

This invention relates to new 11-benzaldoxime-estra-diene derivatives of the general formula I

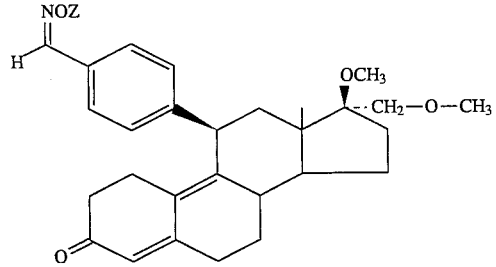

Formula I wherein Z is —CO—CH$_3$, —CO—O—C$_2$H$_5$, —CO—NH-phenyl, —CO—NH—C$_2$H$_5$, —CO—C$_2$H$_5$, —CH$_3$, or —CO-phenyl and their pharmaceutically acceptable salts, a method for their production, and pharmaceuticals containing such compounds. The compounds of the general formula I are produced by esterifying or etherizing a compound of the general formula II

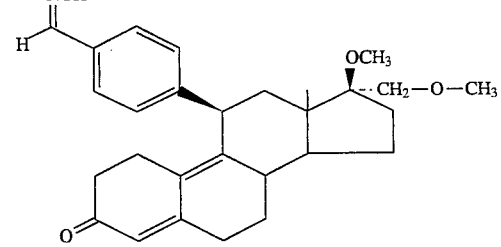

Formula II The compounds described show strong antigestagenic effects combined with reduced glucocorticoid activity.

4 Claims, No Drawings

11-BENZALDOXIME-17β-METHOXY-17α-METHOXYMETHYL-ESTRASDIENE DERIVATIVES, METHODS FOR THEIR PRODUCTION AND PHARMACEUTICALS CONTAINING SUCH COMPOUNDS

DESCRIPTION

This invention relates to new 11-benzaldoxime-estradiene derivatives, methods for their production, and pharmaceuticals containing these compounds.

11β-substituted phenyl estratrienes are known. Patent specification EP 057 115 describes the production of 11β-aryl-17α-propinyl estra-4,9-dienes, and patent specification DE 3 504 421 describes the reaction of 11β-(4-formylphenyl) estra-4,9-diene-3-ons with hydroxylamines. Both the 11β-formyl phenylene residue and the 3-keto group are oximated. In addition, syn and anti isomers are formed at C-3. Nothing is known as yet about the effects of the described compounds.

Progesterone is secreted during menstruation, and in large amounts by the ovary and the placenta during pregnancy. Its regulatory significance has perhaps not been clarified in every respect.

What is safely known is that progesterone, together with oestrogenes, produces the cyclic changes in the uterine mucosa during the menstrual cycle and pregnancy. After ovulation, an increased level of progesterone causes the uterine mucosa to adopt a condition that permits the embedding of an embryo (blastocyst). Conservation of the tissues in which the embryo grows is also dependent on progesterone.

A dramatic change in the muscular function of the uterus takes place during pregnancy. Response of the gravid uterine muscle to hormonal and mechanical stimuli that induce labour in the non-gravid state is strongly reduced or non-existent. There can be no doubt that progesterone has a key function here, despite the fact that at certain stages of pregnancy, e.g. shortly before giving birth, there is a high reactivity even at high blood-progesterone concentrations.

Very high progesterone levels are also reflected by other typical processes during pregnancy. The composition of the mammary glands and the obstruction of the cervix until shortly before the date of birth-giving may serve as examples of this.

Progesterone contributes subtly to controlling ovulation processes. It is known that high doses of progesterone have anti-ovulatory qualities. They result from an inhibition of the hypophyseal gonadotropin secretion which is a prerequisite for the maturation of the follicle and for its ovulation. But on the other hand, it can be seen that the comparatively small quantity of progesterone secreted by the maturing follicle plays an active part in preparing and triggering ovulation. Hypophyseal mechanisms (temporary, so-called positive feedback of progesterone to gonadotropin secretion) appear to have a great significance in this respect (Loutradie, D.; Human Reproduction 6, 1991, 1238–1240).

The doubtlessly existing functions of progesterone in the maturing follicle and luteal corpus themselves have been less well analyzed. It can be assumed, eventually, that there are both stimulating and inhibiting effects on endocrinic functions of the follicle and the luteal corpus.

It may also be assumed that progesterone and progesterone receptors are of great importance for pathophysiological processes. Progesterone receptors have been found in endometriotic focuses, but also in tumours of the uterus, the mamma, and the CNS (meningiomas). The role of these receptors in conjunction with the growth behaviour of these pathologically relevant tissues is not necessarily dependent on progesterone levels in the blood. It has been proved that substances characterized as progesterone antagonists such as RU 486=Mifepristone (EP-0 057 115) and ZK 98299= Onapristone (DE-OS-35 04 421) tend to trigger far-reaching functional changes even at negligible levels of progesterone in the blood. It appears to be possible that modifications of the transcriptional effects of the progesterone receptor that is not filled with progesterone are decisive in this respect (Chwalisz, K. et al., Endocrinology, 129, 317–322, 1991).

The effects of progesterone in tissues of the genitals and in other tissue are brought about by interaction with the progesterone receptor. In a cell, progesterone bonds to its receptor with high affinity. This causes changes in the receptor protein: conformational changes, dimerization of 2 receptor units to form one complex, baring of the receptor's DNA bonding place by dissociating a protein (HSP 90), bonding to hormon-responsive DNA elements. Eventually, the transcription of certain genes is regulated. (Gronemeyer, H. et al., J. Steroid Biochem. Molec. Biol. 41, 3–8, 1992).

The effect of progesterone or progesterone antagonists does not only depend on their concentration in the blood. The concentration of receptors in a cell is strongly regulated as well. Oestrogens stimulate the synthesis of progesterone receptors in most tissues. Progesterone inhibits the synthesis of oestrogen receptors and that of its own receptor. It is assumed that this interaction of oestrogens and gestagens goes to explain why gestagens and antigestagens can influence oestrogen-dependent processes without being bonded by the oestrogen receptor. These relations are naturally of great importance for the therapeutical application of antigestagens. These substances appear to be appropriate for directly influencing female reproductive processes, e.g. for preventing nidation after ovulation, or for increasing uterine reactivity to prostaglandins and oxytocin in a later pregnancy, or for achieving metreurysis and cervix softening ("maturing").

Antigestagens inhibit ovulation in various species of subhuman primates. The mechanism of this effect has not yet been elucidated. Among the hypotheses discussed are an inhibition of gonadotropin secretion, and ovarian mechanisms based on disturbing para- and autocrinic functions of progesterone in the ovary.

Antigestagens are capable of modulating or weakening the effects of oestrogens although the majority of them does not have any oestrogen receptor affinity at the cytoplasmic level, and although they can cause an increase of the oestrogen receptor concentration. Similar effects in endometriotic focuses or tumorous tissue equipped with oestrogen and progesterone receptors justify the expectation of a favourable influence on pathologic conditions. Particular advantages with regard to exerting a favourable influence on pathologic conditions such as endometriosis might be achieved if an inhibited ovulation supplemented the inhibiting effects of an antigestagen acting in the tissue. Ovarian hormonal products and their stimulating effect on the pathologically altered tissue would also be reduced by inhibiting ovulation. It would be desirable to inhibit ovulation in severe cases of endometriosis to bring the tissue in the genital tract which would normally be in constant reconstruction, into a reversible state of rest.

A method is being discussed with regard to contraception according to which an antigestagen treatment suppresses ovulation, and secretory transformation of the endometrium is induced by subsequent gestagen treatment. The days of treatment with antigestagens and gestagens and the treatment-free days result in a 28-day cycle with a regular withdrawal bleeding (Baulieu, E. E., Advances in Contraception 7, 345–51, 1991).

Antigestagens can have different hormonal and antihormonal properties. Anti-glucocorticoid properties are of particular therapeutic relevance. These are unfavourable for therapeutical applications mainly aimed at inhibiting progesterone receptors as they have undesired side effects when applied at the dosage required for such therapy which may prevent the application of a therapeutically sensible dose, or require that treatment be discontinued. Partial or complete reduction of glucocorticoid properties is an important prerequisite for a therapy using antigestagens, especially with indications that require therapy over several weeks or months.

It is the purpose of this invention to provide new 11β-benzaldoxime-estra-4,9-diene derivatives of the general formula I

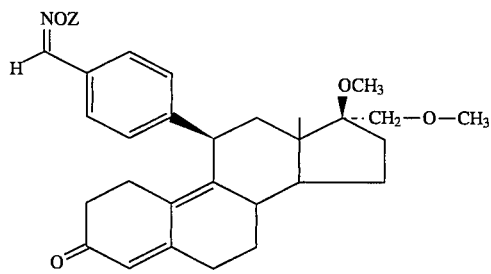

and their pharmaceutically acceptable salts as well as a method for producing them. It is another purpose of this invention to provide pharmaceuticals containing a compound of the general formula I or its pharmaceutically acceptable salt.

In general formula I,

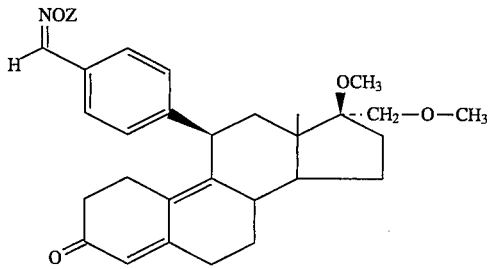

Z is —CO—CH$_3$, —CO—O—C$_2$H$_5$, —CO—NH-phenyl, —CO—NH—C$_2$H$_5$, —CO—C$_2$H$_5$, —CH$_3$, or CO-phenyl.

Preferred compounds according to this invention are:
11β-[4-(acetoximinomethyl)phenyl]-17β-methoxy-17α-methoxymethyl-estra-4,9-diene-3-on,
11β-{4-[(ethoxycarbonyl)oximinomethyl]phenyl}-17β-methoxy-17α-methoxymethyl-estra-4,9-diene-3-on,
11β-{4-[(ethylaminocarbonyl)oximinomethyl]phenyl}-17β-methoxy-17α-methoxymethyl-estra-4,9-diene-3-on,
17β-methoxy-17α-methoxymethyl-11β-{4-[(phenylaminocarbonyl)oximinomethyl]phenyl}-estra-4,9-diene-3-on,
11β-[4-(propionyloximinomethyl)phenyl]-17β-methoxy-17α-methoxymethyl-estra-4,9-diene-3-on,
11β-[4-(methyloximinomethyl)phenyl]-17β-hydroxy-17α-methoxymethyl-estra-4,9-diene-3-on, and
11β-[4-(benzoyloximinomethyl)phenyl]-17β-hydroxy-17α-methoxymethyl-estra-4,9-diene-3-on.

This invention furthermore relates to a method for producing compounds of the general formula I and their pharmaceutically acceptable salts, characterized in that a compound of the general formula II

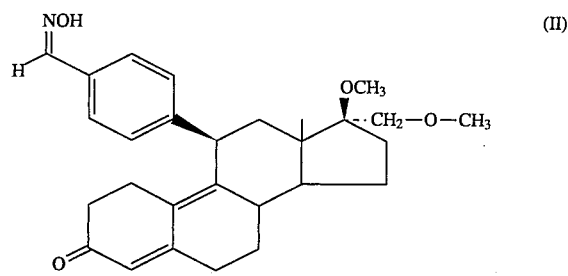

is esterified or etherified, and, if required, the resulting compound is salified.

Manufacturing of the compounds of the general formula I by esterification, etherification, or urethane formation may be carried out in a generally known way using acylating agents such as acid anhydrides or acid chlorides in the presence of bases, preferably pyridine, etherification using methyl iodide in the presence of bases, preferably potassium tert. butanolate, or using diazomethane in methanol; urethane formation by reacting with alkyl or aryl isocyanates in inert solvents, preferably toluene, or by reacting carbamoylchlorides in the presence of bases, preferably triethylamine.

The parent compound of the general formula II is manufactured from 5α,10α-epoxide III

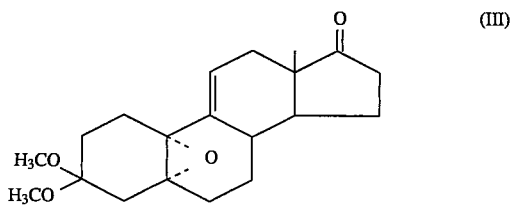

[cf., for example, Nédélec Bull. Soc. chim. France (1970), 2548].

Introduction of the phenyl residue to the 11β position while forming a Δ9(10),5α hydroxy structure IV is achieved by a Cu(I) salt catalyzed Grignard reaction (Tetrahedron Letters 1979, 2051) with a p-bromobenzaldehyde ketal, preferably p-bromobenzaldehyde dimethyl ketal at temperatures between 0° C. and 30° C.

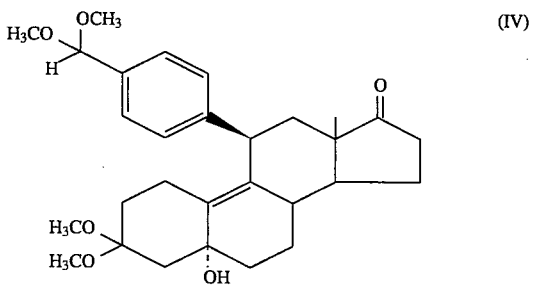

The —CH$_2$—O—CH$_3$ group is introduced to the 17 position in a generally known way via the spiroepoxide V by reacting with trimethyl sulfonium iodide and potassium tert. butanolate in dimethyl sulfoxide [Hübner et al.; J. prakt. Chem. 314, 667 (1972); Arzneim. Forsch. 30, 401 (1973)] and

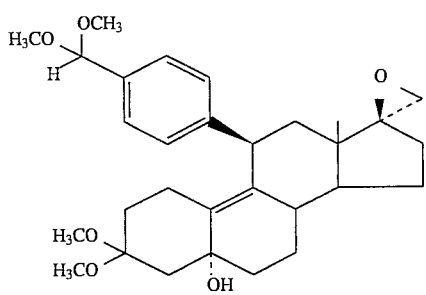

(V)

subsequent ring opening using alcoholares [Ponsold et al.; Z. Chem. 11, 106 (1971)]. The resulting 17α-CH$_2$—O—CH$_3$ compounds VI

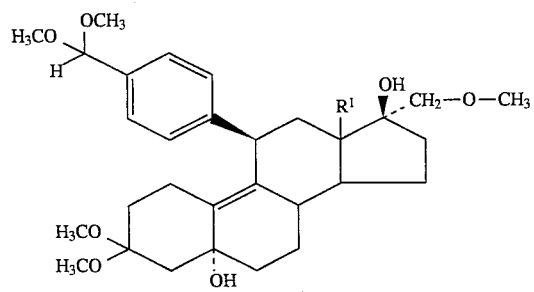

(VI)

may either be decomposed into their respective aldehydes by acid hydrolysis, preferably using toluene-p-sulfonic acid in acetone (Teutsch et al. DE 2801416), or be converted, following etherification of the free hydroxyl groups with alkyl halogenides in the presence of potassium tert. butanolate, first into 5α,17β diethers (Kasch et al. DD 290 893) which are then transformed into their respective aldehydes by acid hydrolysis, preferably using toluene-p-sulfonic acid in acetone; the aldehydes thus obtained are converted into compounds of the general formula II by reacting them with hydroxylamine.

The resulting compound of the general formula I according to the invention is converted, if required, into an acid addition salt, preferably a salt of a physiologically compatible acid. Common physiologically compatible anorganic and organic acids are, for example, hydrochloric acid, hydrobromic acid, phosphoric acid, sulfuric acid, oxalic acid, maleic acid, fumaric acid, lactic acid, tartaric acid, malic acid, citric acid, salicylic acid, adipic acid, and benzoic acid. Other acids that can be used are described, for example, in *Fortschritte der Arzneimittelforschung*, vol. 10, pp. 224–225, Birkhäuser Verlag, Basel and Stuttgart, 1966, and Journal of Pharmaceutical Sciences, vol. 66, pp. 1–5 (1977).

Acid addition salts are normally obtained in a generally known way by mixing the free base or its solutions with the respective acid or its solutions in an organic solvent, for example, a lower alcohol such as methanol, ethanol, n-propanol or isopropanol, or a lower ketone such as acetone, methylethyl ketone or methyl isobutyl ketone, or an ether such as diethyl ether, tetrahydrofurane or dioxane. Compositions of the above-mentioned solvents may be used for improved crystallizing. In addition, physiologically compatible hydrous solutions of acid addition salts Of the compound according to formula I may be produced in a hydrous acidic solution.

The acid addition salts of compounds of the general formula I can be converted into a free base in a generally known way, e.g. using alkalies or ion exchangers. Other salts can be obtained by reacting this free base with anorganic or organic acids, especially acids suited for forming pharmaceutically acceptable salts. These and other salts of the new compound, such as its picrate, may be used to purify the free base: the free base is converted into a salt, the salt is separated, and the base released from the salt again.

Another object of this invention are pharmaceuticals designed for oral, rectal, subcutaneous, intravenous or intramuscular applications that contain as an active ingredient, apart from the usual substrates and diluents, a compound according to the general formula I or its acid addition salt.

The pharmaceuticals of the invention are produced in a known way using the usual solid or liquid substrates or diluents and the common adjuvants used in pharmaceutical engineering and with an appropriate dosage depending on the intended mode of application. Preferred formulations are those forms suitable for oral administration, for example, tablets, film tablets, dragées, capsules, pills, powder, solutions, suspensions, or depot forms.

Consideration may be given also to parenteral formulations such as injection solutions. Suppositories represent another form of application.

Tablets may be obtained, for example, by intermixing the active substance with known adjuvants, for example, inert diluents such as dextrose, sugar, sorbitol, mannite, polyvinylpyrrolidone, blasting agents such as maize starch or alginic acid, binders such as starch or gelatin, lubricants such as magnesium stearate or talcum and/or materials by which to produce a depot effect, such as carboxyl polymethylene, carboxymethyl cellulose, cellulose acetate phthalate or polyvinyl acetate. Tablets may consist of several layers.

Dragées may be produced accordingly by coating cores manufactured in analogy to tablet manufacture using agents generally applied to dragée coating, for example, polyvinylpyrrolidone or shellac, Arabic gum, talcum, titanium dioxide, or sugar. The coating of the dragée may also consist of several layers in which the adjuvants mentioned in the paragraph on tablets can be used.

Solutions or suspensions containing the active agent of the invention may additionally contain flavour-enhancing substances such as saccharin, cyclamate or sugar, or aromatic substances such as vanillin or orange extract. They may also contain suspension-supporting adjuvants such as sodium carboxymethyl cellulose, or preservatives such as p-hydroxybenzoates. Capsules containing active substances may be produced, for example, by mixing the active substance with an inert substrate such as lactose or sorbitol, and encapsulating such mixture in gelatin capsules.

Appropriate suppositories may be made by mixing the active substance with the suitable substrates, such as neutral fats or polyethylene glycol and their derivatives.

The 11β-substituted benzaldoxime-estra-4,9-dienes of the invention are antigestagenic substances that combine, if compared with RU 486, superior in-vivo acting potential (cf. table 2) with a significantly reduced anti-glucocorticoid activity, which has been proved by the reduced bonding to glucocortinoid receptors (cf. table 1).

TABLE 1

Receptor bonding of selected substances listed in Examples 1 and 2

| Compound acc. to Example | Relative molar bonding affinity (RBA) [%] for the glucocorticoid receptor (dexamethasone = 100%) |
|---|---|
| 1 (J914) | 73 |
| 2 (J900) | 66 |

TABLE 1-continued

Receptor bonding of selected substances listed in Examples 1 and 2

| Compound acc. to Example | Relative molar bonding affinity (RBA) [%] for the glucocorticoid receptor (dexamethasone = 100%) |
|---|---|
| compared with | |
| RU 486 (mifepristone) | 685 |
| ZK 98299 (onapristone) | 39 |

This combination of properties of the antigestagens according to the invention promises superior inhibition of progesterone while at the same time reducing anti-glucocorticoid activity. This advantage is of particular relevance for indications that require excellent compatibility because of the duration of treatment. During the menstrual cycle, uterine weight is decisively influenced by the circulating oestrogen. Reduced uterine weights reflect an inhibition of this oestrogenic function. The inhibition of uterine weight during the menstrual cycle determined in guinea pigs is superior to RU 486 and points to (indirect) anti-oestrogenic properties of the compounds according to the invention. The respective effects promise the exertion of a particularly favourable influence on pathologically modified tissues in which oestrogens stimulate growth (endometriotic focuses, myomas, mammary and genital carcinomas, benign prostatic hypertrophy).

TABLE 2

Early abortive effect of RU 486 and J 914 (Example 1) and J 900 (Example 2) in the rat after subcutaneous application from the 5th to 7th day of pregnancy (dose 0.2 ml/animal/day in benzylbenzoate/castor oil [1 + 4 v/v])

| Group, substance | Dose (mg/animal/ day) | complete gravidity inhibition+ N*/N | % | ED 50++ (mg/animal/ day) |
|---|---|---|---|---|
| vehicle | — | 0/25 | 0 | — |
| RU 486 | 3.0 | 5/5 | 100 | |
| | 1.0 | 2/5 | 40 | 1.1 |
| | 0.3 | 0/5 | 0 | |
| J 900 | 1.0 | 9/10 | 90 | 0.6 |
| | 0.3 | 0/5 | 0 | |
| J 914 | 3.0 | 5/5 | 100 | |
| | 1.0 | 7/10 | 70 | 0.6 |
| | 0.3 | 1/5 | 20 | |
| | 0.1 | 0/6 | 0 | |

+empty uteri
N number of inseminated females
N* number of females not pregnant
++graphic determination The following examples explain the invention.

EXAMPLES 180 mg of 11β-[4-(hydroximinomethyl)phenyl]-17β-methoxy-17α-methoxymethyl-estra-4,9-diene-3-on are acetylated in 5 ml of acetic anhydride/pyridine (1:1). After adding water, the batch is three times extracted with acetic ester. The organic phase is washed with dilute hydrochloric acid and water, dried above sodium sulfate, and concentrated by evaporation under reduced pressure. The yield is 172 mg of crude product that is purified by preparative thin-layer chromatography using silica gel $PF_{245+366}$ and a toluene/acetone solvent system at a concentration of 4:1.

Yield: 115 mg of 11β-[4-(acetyloximinomethyl)phenyl]-17β-methoxy-17α-methoxymethyl-estra-4,9-diene-3-on. The product crystallizes from acetic ester.

Melting point: 115°–120° C. (acetic ester) $α_D$=+218° ($CHCl_3$)

IR spectrum in KBr ($cm^{-1}$): 1754 (OAc); 1654 (C═C—C═C—C═O); 1602 (phenyl)

UV spectrum in MeOH: $λ_{max}$=271 nm $ε$=28 157 $λ_{max}$=297 nm $ε$=26 369

$^1$H-NMR spectrum in $CDCl_3$ [δ, ppm]: 0.511 (s, 3H, H-18); 2.227 (s, 3H, $OCOCH_3$); 3.247 (s, 3H, 17β-$OCH_3$); 3.408 (s, 3H, 17α-$CH_2OCH_3$); 3.386, 3.431, 3.544, 3.580 (m, 2H, $CH_2OCH_3$); 4.399 (d, 1H, J=7.2 Hz, H-11α); 5.785 (s, 1H, H-4); 7.242, 7.266, 7.618, 7.647 (m, 4H, AA'BB' system of aromatics protons); 8.315 (s, 1H, C$\underline{H}$=NOAc)

MS m/e: 446 $C_{28}H_{32}NO_4$ $M^+$–$CH_2OCH_3$+

EXAMPLE 2

0.3 ml of chloroethyl formate are dripped into 210 mg of 11β-[4-(hydroximinomethyl)phenyl]-17β-methoxy-17α-methoxymethyl-estra-4,9-diene-3-on in 5 ml of pyridine while cooling with water. A white sediment forms. The batch is watered after 30 minutes, which results in a solution in which a white sediment settles down that is filtered off by suction and washed with water. Yield after drying: 133 mg. The aqueous phase is extracted with chloroform, washed with dilute hydrochloric acid and water, dried, and concentrated by evaporation under reduced pressure. Yield: 66 mg. Both solids are united and purified by preparative thin-layer chromatography using silica gel $PF_{245+366}$ and a toluene/acetone solvent system at a concentration of 4:1.

Yield: 150 mg of 11β-[4-(ethoxycarbonyloximinomethyl)phenyl]-17β-methoxy-17α-methoxymethyl-estra-4,9-diene-3-on which are recrystallized from acetone/hexane.

Melting point: 137°–148° C. $α_D$=+204° ($CHCl_3$)

UV spectrum in MeOH: $λ_{max}$=270 nm $ε$=27 094 $λ_{max}$=297 nm $ε$=25 604

$^1$H-NMR spectrum in $CDCl_3$ [δ, ppm]: 0.507 (s, 3H, H-18); 1.383 (t, 3H, J=7.0 Hz, $OCH_2CH_3$); 3.246 (s, 3H, 17β-$OCH_3$); 3.410 (s, 3H, 17α-$CH_2OCH_3$); 3.39–3.56 (m, 2H, $CH_2OCH_3$); 4.35 (d, 1H, J=7.0 Hz, H-11α); 5.784 (s, 1H, H-4); 7.23, 7.26, 7.61, 7.64 (m, 4H, AA'BB' system of aromatics protons); 8.303 (s, 1H, C$\underline{H}$=NR)

MS m/e: 431. 24701 $C_{28}H_{32}NO_3$ $M^+$–$C_2H_5OCOOH$

EXAMPLE 3

190 mg of 11β-[4-(hydroximinomethyl)phenyl]-17β-methoxy-17α-methoxymethyl-estra-4,9-diene-3-on are suspended in 10 ml of toluene. 0.5 ml of phenyl isocyanate and 1 ml of triethyl amine are added subsequently. The batch is agitated at room temperature for 3 hours and refluxed for 2 hours. The white sediment is filtered off by suction, and the solvent concentrated by evaporation under reduced pressure. Thus 310 mg of a light brown solid are obtained which is purified by preparative thin-layer chromatography using silica gel $PF_{245+366}$ and a toluene/acetone solvent system at a concentration of 9:1.

65 mg of 17β-methoxy-17α-methoxymethyl-11β-{4-[(phenyl-amino-carbonyl)oximinomethyl)]phenyl}-estra-4,9-diene-3-one are isolated Melting point: 241°–246° C. (acetone) $\alpha_D$=+178° (CHCl$_3$)

U/V spectrum in MeOH: $\lambda_{max}$=238 nm $\epsilon$=29 444 $\lambda_{max}$= 300 nm $\epsilon$=29 649

$^1$H-NMR spectrum in CDCl$_3$ [δ, ppm]: 0.474 (s, 3H, H-18); 3.245 (s, 3H, 17β-OC$\underline{H}_3$); 3.405 (s, 3H, 17α-CH$_2$OC$\underline{H}_3$); 3.406–3.545 (m, 2H, ABX system, 17α-C$\underline{H}_2$OCH$_3$); 4.413 (d, 1H, J=6.8 Hz, H-11α); 5.797 (s, 1H, H-4); 7.264 (m, 5H, aromatic), 7.272, 7.293, 7.548, 7.575 (m, 4H, AA'BB' system of aromatics protons); 8.0 (s, 1H, C$\underline{H}$=N—)

MS m/e: 431.24249 C$_{28}$H$_{33}$NO$_3$ M$^+$–C$_6$H$_5$CNO+H$_2$O

EXAMPLE 4

708 mg of 11β-[4-(hydroximinomethyl)phenyl]-17β-methoxy-17α-methoxymethyl-estra-4,9-diene-3-on are dissolved in 15 ml of toluene. 1.5 ml of ethyl isocyanate and 3 ml of triethyl amine are added subsequently. The batch is agitated at room temperature for 6 hours and allowed to stand overnight. Then 20 ml of aqueous ammonium solution are added, the phases are separated, extracted with toluene, washed in water, aqueous ammonium solution, and water, dried above sodium sulfate and concentrated by evaporation under reduced pressure. Thus 800 mg of a bright yellow solid are obtained which is purified by preparative thin-layer chromatography using silica gel 60 PF$_{254+366}$ and a toluene/acetone solvent system at a concentration of 9:1.

610 mg of 11β-{4-[(ethylaminocarbonyl)oximinomethyl)]-phenyl}-17β-methoxy-17α-methoxymethyl-estra-4,9-diene-3-on are isolated.

Melting point: 142°–147° C. photodecomposition (ether/acetone/hexane)

$^1$H-NMR spectrum in CDCl$_3$ [δ, ppm]: 0.522 (s, 3H, H-18); 1.241 (t, 3H, J=7.5 Hz, NHCH$_2$C$\underline{H}_3$); 3.253 (s, 3H, 17β-OC$\underline{H}_3$); 3.415 (s, 3H, 17α-CH$_2$OC$\underline{H}_3$); 3.366–3.574 (m, 4H, ABX system, 17α-C$\underline{H}_2$OCH$_3$, NHC$\underline{H}_2$CH$_3$); 4.410 (d, 1H, J=7.2 Hz, H-11α); 5.790 (s, 1H, H-4); 6.238 (m, 1H, NHCO), 7.258, 7.286, 7.561, 7.589 (m, 4H, AA'BB' system of aromatics protons); 8.294 (s, 1H, C$\underline{H}$=N—)

EXAMPLE 5

500 mg of 11β-[4-(hydroximinomethyl)phenyl]-17β-methoxy-17α-methoxymethyl-estra-4,9-diene-3-on are agitated subject to inert gas for 2.5 hours in 4 ml of propionic acid anhydride/pyridine 1:1 (v:v). The mixture is poured into iced water, and the sticky substance is extracted with chloroform. The organic phase is washed with dilute hydrochloric acid and water, dried above sodium sulfate, and concentrated by evaporation under reduced pressure.

The bright yellow foam is purified using chromatography and recrystallized from acetic ester. Yield: 306 mg of 11β-[4-(propionyloximinomethyl)phenyl]-17β-methoxy-17α-methoxymethyl-estra-4,9-diene-3-on.

Melting point: 110°–114° C. (acetic ester)

$^1$H-NMR Spectrum in CDCl$_3$ [δ, ppm]: 0.515 (s, 3H, H-18); 1.241 (t, 3H, J=7.6 Hz, OCOC$\underline{H}_2$C$\underline{H}_3$); 3.253 (s, 3H, 17β-OC$\underline{H}_3$); 3.415 (s, 3H, 17α-CH$_2$OC$\underline{H}_3$); 3.4–3.6 (m, 2H, ABX system, 17α-C$\underline{H}_2$OCH$_3$); 4.128 (d, 1H, J=7.2 Hz, H-11α); 5.790 (s, 1H, H-4); 7.244, 7.271, 7.627, 7.655 (m, 4H, AA'BB' system of aromatics protons); 8.322 (s, 1H, C$\underline{H}$=N—)

EXAMPLE 6

An etherial diazomethane solution is added while cooling with ice to 170 mg of 11β-[4-(hydroximinomethyl)phenyl] -17β-methoxy-17α-methoxymethyl-estra-4,9-diene-3-on until the mixture takes on a slight yellow colouring. The batch is agitated for 2 hours at 5° C., and dilute sodium hydroxide solution is added. Then the mixture is extracted with ether, washed neutrally, and dried above sodium sulfate. The organic phase is evaporated under reduced pressure. The yellow resin is purified by preparative thin-layer chromatography using silica gel 60 PF$_{254+366}$ and a toluene/acetone solvent system at a concentration of 4:1.

Yield: 110 mg of 11β-[4-(methoximinomethyl)phenyl]-17β-hydroxy-17α-methoxymethyl-estra-4,9-diene-3-on in the form of colourless lamellae.

Melting point: 83°–89° C. $\alpha_D$=+197° (CHCl$_3$) IR spectrum in CHCl$_3$ (cm$^{-1}$): 1700 (C=NOCH$_3$); 1649 (C=C—C=C—C=O); 1590 (aromatic)

UV spectrum in MeOH: $\lambda_{max}$=275 nm $\epsilon$=23 098 $\lambda_{max}$=300 nm $\epsilon$=22 872

$^1$H-NMR spectrum in CDCl$_3$ [δ, ppm]: 0.529 (s, 3H, H-18); 3.247 (s, 3H, 17β-OC$\underline{H}_3$); 3.408 (s, 3H, 17α-CH$_2$OC$\underline{H}_3$); 3.39–3.598 (m, 2H, ABX system, 17α-C$\underline{H}_2$OCH$_3$); 4.381 (d, 1H, J=7.5 Hz, H-11α); 5.773 (s, 1H, H-4); 7.173, 7.201, 7.463, 7.491 (m, 4H, AA'BB' system of aromatics protons); 8.023 ( s, 1H, C$\underline{H}$phenyl )

EXAMPLE 7

A filtered mixture of 2 ml of benzoyl chloride and 3 ml of pyridine is added to 500 mg of 11β-[4-(hydroximinomethyl)phenyl]-17β-methoxy-17α-methoxymethyl-estra-4,9-diene-3-on. After 2 hours, the mixture is stirred into 150 ml of iced water. The steroid precipitates as a sticky substance. 5 ml of hydrochloric acid are added, and the mixture is taken up in acetic ester. The phases are separated, the organic phase is washed in aqueous bicarbonate solution and water, dried above sodium sulfate, filtered off, and evaporated under reduced pressure. The yellow oil (1.57 g) is liberated from nonpolar products using chromatography on 40 g of silica gel 60 and a toluene/acetic ester gradient. The main fraction (0.7 g) is purified by preparative thin-layer chromatography using silica gel 60 PF$_{254+366}$ and a chloroform/acetone solvent system. 410 mg of a colourless foam is obtained that is recrystallized from methanol.

Yield: 263 mg of 11β-[4-(benzoyloximinomethyl)phenyl] -17β-methoxy-17α-methoxymethyl-estra-4,9-diene-3-on as colourless foam.

Melting point: 115°–122° C. (methanol) $\alpha_D$=+216° (CHCl$_3$)

UV spectrum in MeOH: $\lambda_{max}$=279 nm $\epsilon$=33 720 $\lambda_{max}$= 299 nm $\epsilon$=30 120

$^1$H-NMR spectrum in CDCl$_3$ [δ, ppm]: 0.527 (s, 3H, H-18); 3.253 (s, 3H, 17β-OC$\underline{H}_3$); 3.415 (s, 3H, 17α-CH$_2$OC$\underline{H}_3$); 3.403–3.598 (m, 2H, ABX system, 17α-C$\underline{H}_2$OCH$_3$); 4.416 (d, 1H, J=7.2 Hz, H-11α); 5.792 (s, 1H, H-4); 7.299–7.615 (m, 5H, aromatics protons, CO phenyl); 7.701, 7.729, 8.111, 8.140 (m, 4H, AA'BB' system of aromatics protons); 8.520 (s, 1H, C$\underline{H}$phenyl)

EXAMPLE 8

Measurement of bonding affinity for receptors

Receptor bonding affinity was determined by competitive bonding of a specifically binding $^3$H labelled hormone (tracer) and the compound to be tested to receptors in the cytosol from animal target organs. It was tried to obtain receptor saturation and a balanced reaction. The following incubation conditions were selected:

Glucocorticoid receptor: thymus cytosol of the adrenalectomized rat, thymi kept at −30° C., buffer: TED. Tracer: $^3$H-dexamethasone, 20 nM; reference substance: dexamethasone.

After an incubation period of 18 hours at 0°–4° C., bonded and free steroid was separated by mixing in active carbon/dextrane (1%/0.1%), centrifuging off and measuring the bonded $^3$H activity in the supernatant.

The $IC_{50}$ for the compound to be tested and for the reference substance were determined from measurements in series of concentrations. The quotient of both values (x 100%) is the relative molar bonding affinity.

EXAMPLE 9

Inhibition of early gravidity in the rat:

Female rats are mated in the pro-oestrus. If semen is found in the vaginal smear on the next day, this day is counted as day 1 (=d1) of the gravidity. Treatment with the test substance or vehicle is applied on d5–d7, autopsy is carried out on d9. The substances are injected subcutaneously in 0.2 ml of vehicle (benzyl benzoate/castor oil 1+4). The rate of fully inhibited gravidities found in various groups can be seen from table 1. A superior inhibition capability of nidation was found for J 917 and J 900 as compared to RU 486.

What we claim is:

1. A 11β-benzaldoxime-estra-4,9-diene-derivative of the general formula I:

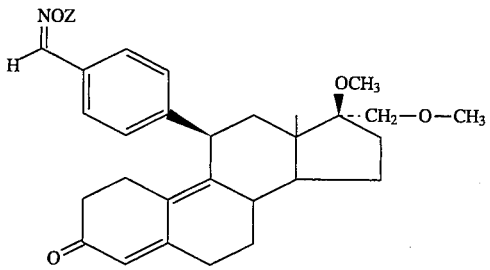

Formula I wherein,

Z is —CO—CH$_3$, —CO—O—C$_2$H$_5$, —CO—NH-phenyl, —CO—NH—C$_2$H$_5$, —CO—C$_2$H$_5$, —CH$_3$, or CO-phenyl, and pharmaceutically acceptable salts thereof.

2. A compound according to claim 1, selected from the group consisting of:

11β-[4-(acetoximinomethyl)phenyl]-17β-methoxy-17α-methoxymethyl-estra-4,9-diene-3-on, 11β-{4-[(ethoxycarbonyl)oximinomethyl]phenyl}-17β-methoxy-17α-methoxymethyl-estra-4,9-diene-3-on, 11β-{4-(ethylaminocarbonyl)oximinomethyl]phenyl}-17β-methoxy-17α-methoxymethyl-estra-4,9-diene-3-on, 17β-methoxy-17α-methoxymethyl-11β-{4-[(phenylaminocarbonyl)oximinomethyl]phenyl}-estra-4,9-diene-3-on, 11β-[4-(propionyloximinomethyl)phenyl]-17β-methoxy-17α-methoxymethyl-estra-4,9-diene-3-on, 11β-[4-(methyloximinomethyl)phenyl]-17β-hydroxy-17α-methoxymethyl-estra-4,9-diene-3-on, and 11β-[4-(benzoyloximinomethyl)phenyl]-17β-hydroxy-17α-methoxymethyl-estra-4,9-diene-3-on.

3. A pharmaceutical composition, characterized in that it contains at least one compound according to claim 1 or 2.

4. A pharmaceutical composition, comprising a pharmaceutically effective concentration of a compound according to claim 1 or 2, or salts or mixtures thereof, in a pharmaceutically acceptable carrier.

* * * * *